United States Patent
Brummund et al.

(10) Patent No.: US 12,251,180 B2
(45) Date of Patent: *Mar. 18, 2025

(54) OPTICAL CAMERA POSITIONING TOOL

(71) Applicant: MedTech S.A., Montpellier (FR)

(72) Inventors: Martin Kristian Eckhard Brummund, Montreal (CA); Jean-Sebastien Merette, Mont-St-Hiliare (CA); Mohamed Yessine Yengui, Saint-Leonard (CA)

(73) Assignee: MedTech S.A., Montpellier (FR)

( * ) Notice: Subject to any disclaimer, the term of this patent is extended or adjusted under 35 U.S.C. 154(b) by 177 days.

This patent is subject to a terminal disclaimer.

(21) Appl. No.: 17/964,657

(22) Filed: Oct. 12, 2022

(65) Prior Publication Data
US 2023/0058564 A1    Feb. 23, 2023

Related U.S. Application Data

(63) Continuation of application No. 16/298,626, filed on Mar. 11, 2019, now Pat. No. 11,490,969.
(Continued)

(51) Int. Cl.
*A61B 34/30* (2016.01)
*A61B 34/20* (2016.01)
(Continued)

(52) U.S. Cl.
CPC .............. *A61B 34/30* (2016.02); *A61B 34/20* (2016.02); *F16M 11/06* (2013.01);
(Continued)

(58) Field of Classification Search
CPC . A61B 34/30; A61B 34/20; A61B 2034/2048; A61B 2034/252;
(Continued)

(56) References Cited

U.S. PATENT DOCUMENTS 6,187,018 B1    2/2001    Sanjay-Gopal et al.
9,308,050 B2    4/2016    Kostrzewski et al.
(Continued)

FOREIGN PATENT DOCUMENTS

CN        106681108 A      5/2017

OTHER PUBLICATIONS

U.S. Appl. No. 16/298,626 U.S. Pat. No. 11,490,969, filed Mar. 11, 2019, Optical Camera Positioning Tool.
(Continued)

*Primary Examiner* — Keith M Raymond
*Assistant Examiner* — Patrick M Mehl
(74) *Attorney, Agent, or Firm* — SCHWEGMAN LUNDBERG & WOESSNER, P.A.

(57) ABSTRACT

A system and method may be used to position or orient a camera within a surgical field. A method may include generating a graphical user interface including a first set of instructions to reposition the camera, and determining whether the camera is within a target volume location. The method may include automatically outputting an indication when the camera is within the target volume location. The method may include outputting a second set of instructions for display on the graphical user interface to align a laser, coupled to or integrated into the camera, to the tracker by changing an angle of the camera.

21 Claims, 7 Drawing Sheets

Related U.S. Application Data

(60) Provisional application No. 62/646,431, filed on Mar. 22, 2018.

(51) Int. Cl.
  *F16M 11/06*   (2006.01)
  *G03B 17/56*   (2021.01)
  *G06F 9/30*    (2018.01)
  *H04N 23/60*   (2023.01)

(52) U.S. Cl.
  CPC ....... *G03B 17/561* (2013.01); *G06F 9/30003* (2013.01); *H04N 23/60* (2023.01)

(58) Field of Classification Search
  CPC .............. A61B 2034/256; A61B 34/25; A61B 2034/2057; A61B 2034/254; A61B 2034/258; A61B 2090/3983; A61B 90/13; F16M 11/06; F16M 11/2035; F16M 11/24; F16M 11/12; F16M 11/18; F16M 11/2092; F16M 11/42; G03B 17/561; G03B 15/14; G06F 9/30003; H04N 23/60; H04N 23/62; H04N 23/63; H04N 23/64; H04N 23/695; H04N 23/61
  See application file for complete search history.

(56) References Cited

U.S. PATENT DOCUMENTS

| | | |
|---|---|---|
| 11,490,969 B2 | 11/2022 | Brummund et al. |
| 2014/0327792 A1* | 11/2014 | Mulloni ................ H04N 23/69 348/211.8 |
| 2016/0195856 A1 | 7/2016 | Spero |
| 2017/0143429 A1* | 5/2017 | Richmond ............. A61B 34/37 |
| 2019/0254754 A1 | 8/2019 | Johnson et al. |
| 2019/0290370 A1 | 9/2019 | Brummund et al. |

OTHER PUBLICATIONS

"U.S. Appl. No. 16/298,626, Non Final Office Action mailed Apr. 11, 2022", 7 pgs.

"U.S. Appl. No. 16/298,626, Notice of Allowance mailed Jul. 21, 2022", 5 pgs.

"U.S. Appl. No. 16/298,626, Response filed Jul. 8, 2022 to Non Final Office Action mailed Apr. 11, 2022", 9 pgs.

* cited by examiner

OPTICAL CAMERA POSITIONING TOOL

CLAIM OF PRIORITY

This application is a continuation of U.S. patent application Ser. No. 16/298,626, filed on Mar. 11, 2019, which claims the benefit of U.S. Provisional Patent Application Ser. No. 62/646,431, filed on Mar. 22, 2018, the benefit of priority of each of which is claimed hereby, and each of which is incorporated by reference herein in its entirety.

BACKGROUND

In computer-assisted surgery procedures, an optical tracking system is often used to track various objects, such as patient anatomy, instruments, robotic components, or the like. In an optical tracking system, an optical camera may be used in an operating room to detect reflective trackers for the duration of a procedure. However, a point of view from the optical camera to a tracker may become blocked, necessitating moving the camera while stopping the procedure. Sometimes, it is not clear before the procedure where a line of sight may become blocked. To position a camera, some solutions rely on a user guessing at a location for the camera before the procedure.

Certain solutions may describe an optimal position of the camera in general terms, for example vaguely with respect to an operating room table. The user (e.g., a nurse) is then required to approximate the optimal position of the camera without precise measuring tools and may often be required to move the camera during the surgery, depending on the surgical step, in order for the camera to see all required trackers. These solutions are ineffective, potentially costly, and imprecise.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
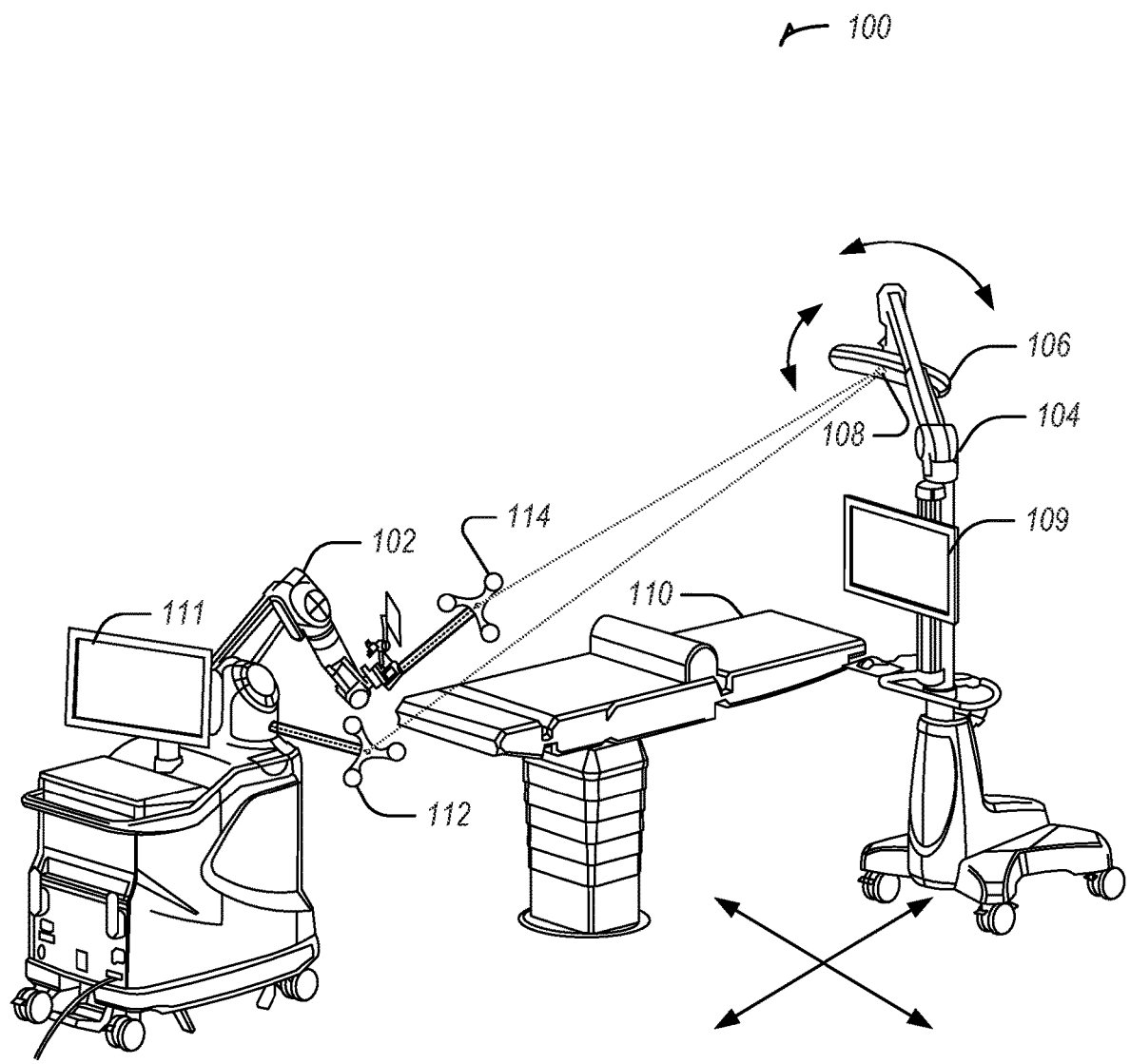
FIG. 1 illustrates a system for positioning or orienting a camera within a surgical field in accordance with some embodiments.

Systems and methods for positioning or orienting a camera within a surgical field are described herein. The systems described herein may include a camera, a user interface or output device (e.g., a display screen, speaker, haptic feedback device, etc.), a camera stand, robotic surgical device, or operating room table, for coordinating the positioning and orientation of the camera within a surgical field (e.g., with respect to the other aspects of the system). In an example, the camera may be used within the surgical field to track one or more objects, such as patient anatomy, an instrument, a tool, the robotic surgical device (or a portion thereof), or the like, such as during a surgical procedure using one or more trackers (e.g., optical trackers).

In order to track the various objects throughout the surgical field, the camera uses a line of sight to a tracking element ("tracker") affixed to each Object. For example, a camera may send tracking data to a computer system based on image information captured by the camera, the image information including a location of a tracker. When the line of sight is obstructed (by a surgeon's arm or a robotic arm for example), tracking signals being transmitted from the tracking element may not be received by the sensors or the camera device. As a result, errors may occur in tracking the objects. In an example in which obstruction occurs, the optical navigation system may be interrupted or discontinued, the surgical procedure stopped, or an error message may be conveyed to the surgeon. These changes may be temporary, such as until the line of sight returns or the system is reset.

A camera device used for tracking within a surgical field may comprise a camera, or a camera mesh that may include plurality of cameras that may be communicatively coupled to a computer image analysis system. By utilizing the camera mesh and the computer image analysis system, one or more objects involved in the surgical procedure may be tracked, such as one or more instruments (e.g., scalpel, implant insertion tools), a body part, or an implant. Tracking an object is not limited to tracking a tool or instrument used by a surgeon. The tracked object may include a body part, such as a leg or hand, the location of an incision, the positioning of a bone inside the body part, or the location of an organ within the patient. In an example, the camera device may track multiple objects concurrently or simultaneously.

The camera device may be configured in many ways for tracking an object or an optical tracker. The camera device may include a depth camera. The camera device may use infrared light to track an object or an optical tracker. In this example, the camera device may be located at a fixed position within a surgical field during a procedure (although, as described below, the camera may rotate when an obstruction is detected or predicted). In an example, the camera device may include stereoscopic cameras (e.g., two cameras within a single housing). Throughout the remainder of the document, camera devices may be referred to simply as a camera Reference to a singular "camera" should be not taken as a limitation or as precluding the discussion as being similarly applicable to camera devices utilizing multiple cameras.

The tracking data imaged by a camera device or collected by an image processing system (e.g., using a processor circuit) may be used to determine a position and an orientation of a tracked object within a virtual three-dimensional coordinate system (e.g., within the surgical field). The tracking data may include the position and direction of the camera device. The image processing system may output the position and the orientation of the tracked object. The output data may include coordinates in a virtual three-dimensional coordinate system. The output may include one or more of the captured images that includes the tracked object. Using the tracking data, a processor may determine that a tracked object is obstructed from the camera's field of view or may predict that a tracked object is going to be or likely to be obstructed in the near future (e.g., within a second, within a few frames, etc.).

Robotics offer a useful tool for assisting the surgeon in the surgical field. A robotic device may assist in the surgical field performing tasks such as biopsies, electrode implantation for functional procedures (e.g., stimulation of the cerebral cortex, deep brain stimulation), open skull surgical procedures, endoscopic interventions, other "key-hole" procedures, arthroplasty procedures, such as total or partial knee replacement, hip replacement, shoulder implant procedures, or the like. In an example, a surgical procedure may use a surgical robot. The surgical robot may include a tracker, which a tracking system may use to determine a relative location of the surgical robot within a coordinate system or a surgical field. The surgical robot may have a different coordinate system or tracking system (e.g., using known movements of the surgical robot to keep track of an end effector of a robotic arm of the surgical robot, which may include using sensors, such as a gyroscope, magnetoscope, accelerometer, etc.). In an example, a processor may be used to coordinate or translate information to or from the surgical robot coordinate or tracking system, to or from a camera-based tracking system.

An optical tracker may be attached to an object for tracking the object in an optical tracking system, in accordance with some examples. The optical tracker may include one or multiple passive reflective fiducial marker components or an active fiducial marker such as a light emitting diode (LED), which may be at a set position on the optical tracker (e.g., relative to one another). The optical tracker may be attached to an object to be detected within the surgical field such as an instrument or a body part (e.g., a bone). The position and orientation of the object relative to the object tracker may be set and recorded such that an optical tracking system may know the position and orientation of the object by determining the position and orientation of the optical tracker ((e.g., using a camera device to capture an image or information about the optical tracker). The position and orientation of the optical tracker may be determined by detecting the one or multiple reflective components and correlating the detected reflective component positioning to the known relative positioning of the multiple reflective components on the optical tracker.

The systems and methods described herein coordinate and manage placement of a camera within a surgical system according to precise location information such that line of sight between the camera and one or more tracked objects is unobstructed, minimized, or both, such as to enhance accuracy and reliability of the tracking and to help avoid or eliminate the need for the camera to be moved during a surgical procedure. The systems and methods described herein may increase operating room or surgical procedure efficiency, as well as surgeon satisfaction with the experience.

FIG. 1 illustrates an example of portions of a system 100 for positioning or orienting a camera within a surgical field in accordance with some embodiments. The system includes a camera 106, which may be affixed to a camera stand 104. A laser 108 or another type of visible directed light emitter may be affixed to the camera 106, embedded within the camera 106, or otherwise coupled to the camera 106 or the camera stand 104. The system 100 may include a robotic surgical device 102, which may be coupled with a tracker 112 affixed to a base of the robotic surgical device 102, or a tracker 114 affixed to an arm of the robotic surgical device 102. FIG. 1 also includes a surgical table 110. Other aspects of a surgical field or operating room may be present and referred to herein, although not depicted in FIG. 1.

The system 100 may help allow for accurate and optimal positioning of the camera 106, such as based on one or more trackers, a surgical procedure, a surgeon preference, an operating room layout, equipment location, a user location, etc. The camera 106 may be positioned with respect to a known tracker (e.g. on a patient, on equipment or a tool, on a robotic surgical device, tracker 112, tracker 114, etc.). In an example, an optimal camera position may be predetermined, such as once at the beginning of a surgical procedure. The optimal camera position may be determined such that it is sufficient for all required steps of the surgical procedure. In an example, the determined optimal camera position may be specific to the operating room environment (e.g., system 100), specific to a surgeon, specific to a procedure, or the like.

To determine the optimal camera position, a target volume may be defined. The target volume may be a region of space (2D or 3D) where the camera 106, the camera stand 104, or either is to be located. For example, the target volume may include floor location with a rotational component to orient the camera 106. In another example, a three-dimensional (3D) space relative to an object may be used to define the target volume. The object in this example may include the base of the robotic surgical device 102, or another fixed or static object (e.g., static during a surgical procedure), such as an object affixed to a reference tracker.

In an example, a tracker is positioned in the operating room on equipment, a tool, a robotic surgical device, patient anatomy, etc. One tracker, in the example shown in FIG. 1, tracker 112 or tracker 114, may be selected as a reference tracker. The reference tracker may be selected according to the particular surgical procedure to be performed, or according to one or more attributes of the object to which the reference tracker is affixed. For example, tracker 112 is selected as the reference tracker in system 100 because it is affixed to the robotic surgical device 102, the base of which is unlikely to move (or move much) during a surgical procedure. In another example, a tracker affixed to the surgical table 110, the floor, the ceiling, etc., may be used as a reference tracker. In yet another example, the tracker 114 affixed to the arm of the robotic surgical device 102 may be used as the reference tracker, which may be more convenient or more easily sighted from the camera 106 by the laser 108.

In yet another example, position information and rotation information may be used to create the target volume as an absolute location or orientation. Here absolute location means within a coordinate system. For example, the operating room or surgical field 100 may have an associated coordinate system. In a specific example, the robotic surgical device 102 may have a robotic coordinate system used to track a robotic arm or other aspect of the robotic surgical device 102. The robotic coordinate system may be used to define the target volume (e.g., a location and orientation or (x,y,z) components within the robotic coordinate system). A control system may be used to convert between the robotic coordinate system and a tracking coordinate system (e.g., for use with the camera 106 to track locations of the tracker 112 or the tracker 114 within the surgical field).

In another example, the tracking coordinate system may be used to define the target volume. For example, the camera 106 may define the location of the tracker 112 as an origin position, and determine its location from that initial origin. Additional information or calibration may be used to determine an orientation (such as described below).

The target volume may be determined using training data. For example, training may be performed by testing locations in various surgical procedures, or changing other variables to determine the optimal location.

In an example, the optimal target volume may be determined based on optical precision of the camera 106. For example, an infrared camera does not necessarily have uniform precision within a visual volume (e.g., edges of image may be less precise than middle), which may also be the camera's field of view. The precision of the visual volume (e.g., an area the camera 106 may "see" within which the camera 106 may track trackers) may be analyzed. The precision analysis may determine a minimum or a maximum distance (or both) from the camera 106 to trackers within the surgical field. The minimum or maximum may then be used to determine locations within the surgical field at which the camera 106 may be placed. One or more additional constraints may be used to further determine the target volume. For example, visual analysis may be used to ensure that all trackers (or locations where all trackers will be throughout a surgical procedure, such as to a certain degree of likelihood) are within the visual volume at the target location. Some candidate target volumes may be eliminated based on one or more spatial constraints, such as a location of another object within the surgical field. For example, the camera 106 may not be able to be positioned within a certain distance of the robotic surgical device 102 (or within a same line of sight), the surgical table 110, a surgeon location, an anesthesiologist location, a tool or instrument location, a wall, etc. In an example, the target volume (and thus the ultimate location of the camera 106) may depend on the location of the robotic surgical device 102 (e.g, offset by a 45 degree or other specified angle, with respect to the operating table 110). In an example in which the surgeon switches sides of the operating table 110 during a surgical procedure (e.g., during a knee arthroplasty, switching knees, such as in a bilateral procedure), the target volume may also move, particularly when the robotic surgical device 102 also switches sides (or changes location). The robotic surgical device 102 may have one or more location specific constraints as well, such as being a certain distance (minimum or maximum or both) from the surgical table 110.

The target volume may be determined after placement of the robotic surgical device 102 (e.g., when using the tracker 112 or the tracker 114 as the reference tracker). For example, the robotic surgical device 102 may be aligned with a femur of a patient or an aspect of the surgical table 110. A robot arm of the robotic surgical device 102 may be pointed down on a patella of the patient (e.g., in the same knee as the femur). This technique may result in the robot being at a 45 degree angle relative to the surgical table 110 and about a foot away. In an example, a drop rod may be used to point to the patella. The drop rod may thread through an opening in a portion of an end effector attached to an arm of the robotic surgical device 102 or an opening in a portion of the arm. In another example, a rigid object may be used. The rigid object may be placed next to or against a portion of the end effector or the arm of the robotic surgical device 102, such as an extrusion. For example, a flat, corner, or T-shaped portion of the end effector, the arm, or the tracker 114 may be used such that the rigid object is placed against the flat, corner, or T-shaped portion.

In an example, after the robotic surgical device 102 is aligned, the camera 106 or the camera stand 104 may be aligned. The robotic surgical device 102 or a portion (e.g., an arm) may be moved before the camera 106 or the camera stand 104 is aligned, for example by moving the arm back a few centimeters to a target position. The target position may be a position determined from an operating position of the arm or the surgical robotic device 102 (e.g., where the arm was aligned using the drop rod, the rigid object, or the like). The target position may be offset from the operating position by a specified distance or angle, such as to enable the camera 106 to be positioned. The target position may be used for example when the laser 108 outputs light in a particular vector, direction, or angle that is fixed.

Determining the minimum or maximum distance for the camera 106 based on the precision of the visual volume may include using an error function or algorithm for detected trackers. In an example, a minimum pixel density of an image may be used for an area of the image taken of the tracker 112 or the tracker 114. In another example, an error rate may be compared to a threshold. The error rate may be based on an image taken by the camera 106 of a tracker. The error comparison may use a root mean square (RMS) error. The RMS error may compare a set of data points taken of the surgical field and compare the set to a set of training data (e.g., previously determined to be optimal or within a tolerance). When the error of the RMS comparison is less than a threshold error (e.g., 0.5 millimeters), then the location of the camera 106 may be determined to be a target volume (or within a possible target volume). The RMS error test may be used, for example, to determine whether the camera 106 is too far away from the tracker 112 or the tracker 114 (although still having line of sight to trackers within the system 100). In an example, the RMS error test may be performed continuously throughout a registration stage (such as described below), such as to ensure that the camera position satisfies the RMS error minimum for each tracker to be tracked within the system 100. For example, as the camera 106 is placed within the target volume but moved further away, the trackers may still be visible during registration process, but the error rate may not satisfy the error rate threshold.

After the target volume is determined, the system 100 may display one or more instructions to a user (e.g., a surgical assistant) to position the camera 106 into the target volume, such as by moving the camera stand 104 and changing an orientation of the camera 106. The instructions may include directing the user to align the laser 108 onto the tracker 112 or the tracker 114. The instructions may be presented on a user interface on a display (e.g., display 109 of the camera stand 104, the display 111 of the robotic surgical device 102, a standalone display, such as one connected to a computer, a mobile device display, or the like), audibly (e.g., over speakers of the robotic display device 102, the camera stand 104, a speaker connected to a computer, etc.), or the like. The user may manually move the camera 106 around the operating room while receiving feedback audibly or on the user interface for which direction to move e continue in that direction, turn left, turn right, etc.). The feedback in the user interface may be provided based on the position and orientation of the reference tracker within the field of view of the camera 106.

The system 100 may present additional directional instructions to tilt, rotate, or move (e.g., up, down, left, right) the camera 106 (e.g., relative to the camera stand 104), and the instructions may update in real-time (e.g., by providing directs to move the camera 106 higher, lower, away, tilt up or down, rotate left or right, move left or right, move forward or backward, etc.). When the system 100 detects that the reference tracker is in the correct position or orientation in the camera field of view, the system 100 may inform the user via the user interface or audibly that the camera 106 is in the correct position and orientation (e.g., within the target volume and oriented correctly relative to the reference tracker).

In another example, after the instructions are used to position the camera 106 or camera stand 104 within the target volume, the laser 108 may be used to target the reference tracker. The user may rotate the camera 106 to align the laser 108 with the reference tracker. The system 100 may present instructions to orient the laser 108 towards the reference tracker, such as to aim within a central portion, a target, a specifically colored portion, or the like of the reference tracker.

In an example, the target volume is specific to a surgeon, surgical field, procedure, camera type, camera stand type, robotic characteristic, or the like. The target volume may be determined according to the specified attributes, or may be reused from a previous set up. The target volume may be stored in a computer of the camera stand 104, the robotic surgical device 102, or a standalone device. A surgeon-specific target volume may be saved based on a surgeon-specific parameter, such as tendencies of a surgeon (e.g., side of the surgical table 110 the surgeon typically uses for a particular procedure, movement tendencies of the surgeon, etc.), height or arm reach of the surgeon, surgical assistants, instrument placement preferences of the surgeon for a particular procedure, portion of a technique performed (e.g., whether the surgeon uses or does not use the robotic surgical device 102 for particular portions of the a surgical procedure such as landmarking, as a cut guide, in a pull test, as a cutting device, etc.), or the like. In an example, a location of the robotic surgical device 102 may determine the target volume. The location of the robotic surgical device 102 may be specific to a surgeon, surgical field, procedure, camera type, camera stand type, robotic characteristic, or the like, thus making the target volume so specific as well.

A procedure-specific target volume may be based on a procedure-specific parameter, such as typical or predicted movement of the surgical robotic arm 102, the surgeon, the patient, or other people within the surgical field, number of trackers needed or used for the procedure, etc. Preferences or constraints may be combined with for a procedure-specific target volume and a surgeon-specific target volume to create a target volume. In an example, the target volume may change location, size, etc. from one procedure to another.

In a surgical procedure that uses optical trackers, such as the tracker 112 or the tracker 114, a registration procedure may be performed at the beginning of the surgical procedure. Registration includes identifying each tracker (e.g., tracker 112 or the tracker 114) throughout the surgical field using the camera 106. The registration identifies a location of each tracker within the camera coordinate system. The registration may include converting the location of a tracker within the camera coordinate system to a robotic coordinate system. Registration is used such that locations of objects (e.g., an instrument, patient anatomy, etc.) are known to the robotic surgical device 102. Registration may include setting an origin, such as a point related to the tracker 112 (e.g, such that the camera coordinate system and the robotic coordinate system share an origin point). During registration, the camera 106 may be monitored (e.g., using an RMS error technique against a threshold) to ensure that the camera 106 does not move outside of the target volume or lose the laser sight to the tracker 112 or the tracker 114. When movement is detected (e.g., someone accidentally bumps the camera stand 104), a user may be notified, such as using a user interface, haptic feedback, audible feedback, etc., and registration may be paused or stopped.

Figure 2:
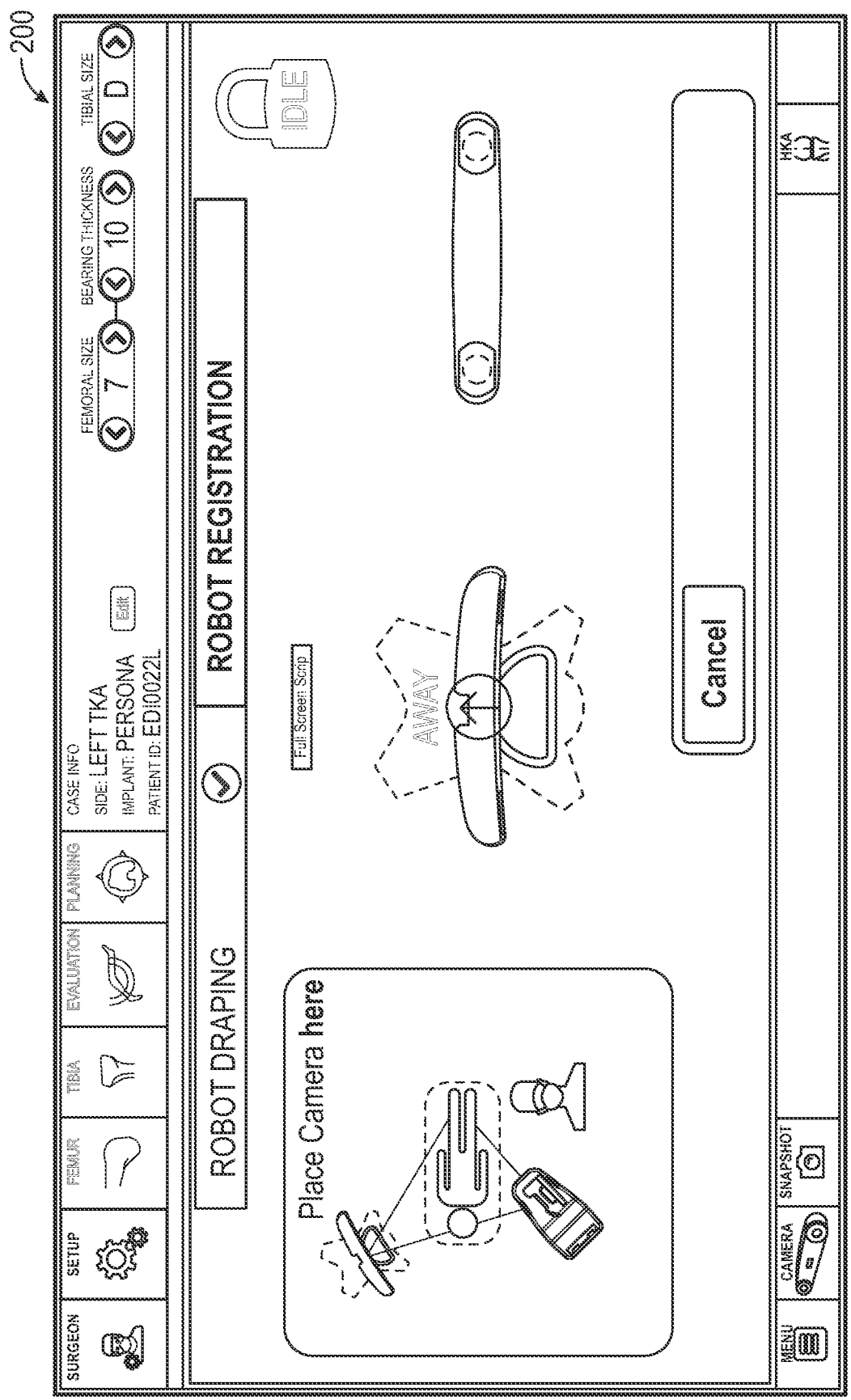
FIGS. 2-3 illustrate one or more graphical user interfaces for providing instructions for positioning or orienting a camera in accordance with some embodiments.
Figure 3:
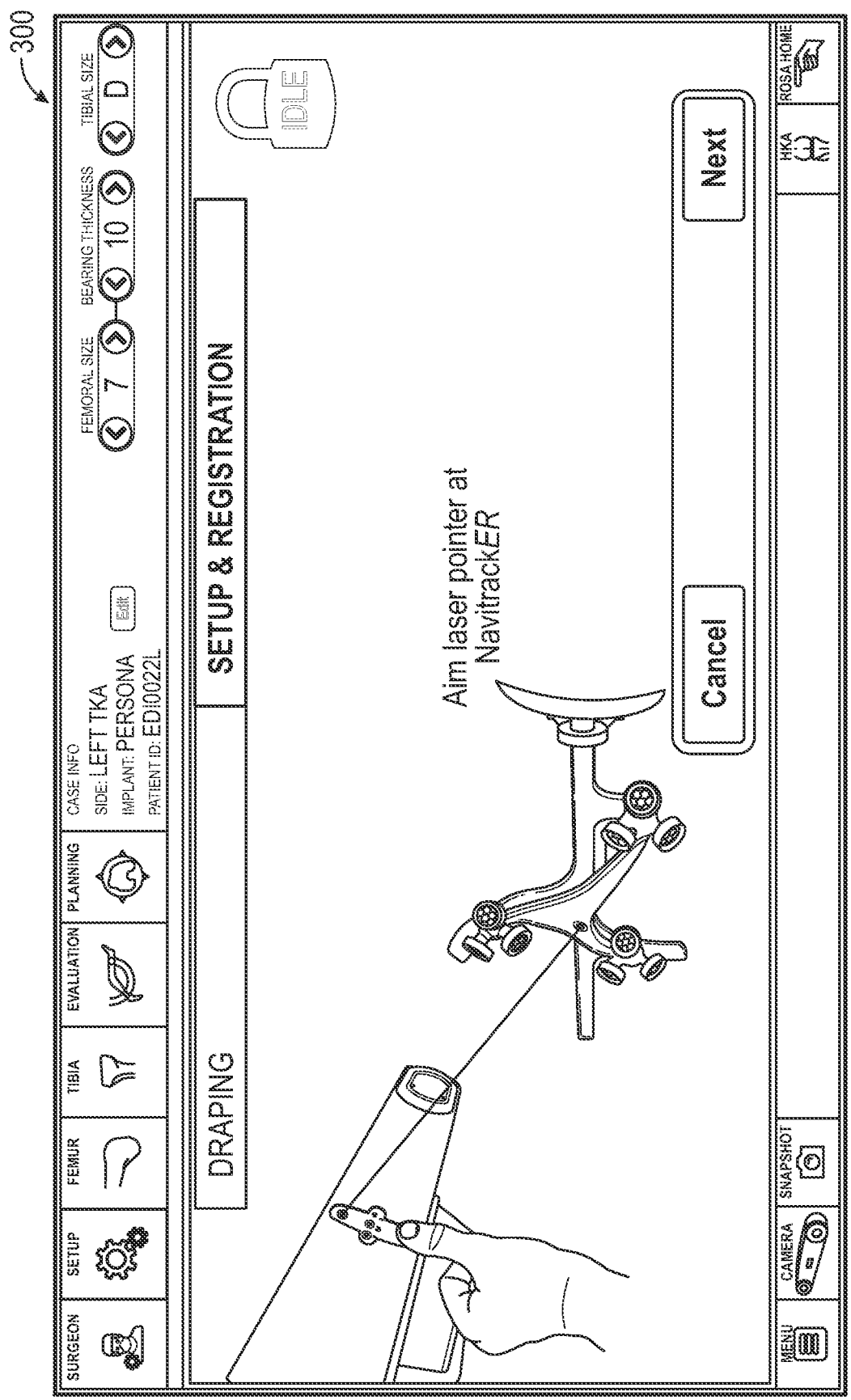

FIGS. 2-3 illustrate one or more graphical user interface display image portions 200-300 for providing instructions for positioning or orienting a camera in accordance with some embodiments. In an example, the user interface portion 200 may be presented with the user interface portion 300. In an example, the user interface portions 200-300 may be generated together, may update, may switch back and forth, may be presented in either order, or may be presented on different display screens.

User interface portion 200 includes instructions directing a user to move a camera stand away from a reference tracker and to change the orientation of a camera, for example towards the floor. In another example, the user interface portion 200 may indicate that the camera stand is to be moved towards the reference tracker or the camera oriented towards the ceiling, or that either is to be turned left or right. In another example, only the towards/away directions may be displayed. The user interface portion 200 may also output audible directions. In an example, the camera or camera stand may generate haptic feedback to indicate the camera or camera stand is close or far, moving in a correct or incorrect direction, or the like.

The user interface portion 200 includes a depiction (e.g., a video or computer-generated graphic) of the surgical field. The depiction may include a location of the target volume and a location of the camera/camera stand. As the user moves the camera/camera stand towards the target volume, the depiction may be updated (e.g., in real-time using feedback from the camera), intuitively showing the user the progress of the camera/camera stand. In an example, the depiction may augment or replace the instructions described above for user interface portion 200. Other audio, haptic, or visual feedback may be generated, such as a blinking light, which blinks faster or slower, or a sound, which beeps faster or slower, depending on whether the user is closing in on the target volume or getting farther away.

In an example, when the camera or the camera stand enters the target volume, the user interface portion 200 may transition automatically to the user interface portion 300. User interface portion 300 illustrates a technique for the user to point the laser (located in, on, or coupled to the camera) towards the reference tracker. The instructions may also be audible. When the user has oriented the laser on the reference tracker, the user may select the "next" button (or similar) on the user interface portion 300 to proceed to a next operation or receive further instructions. In an example, further instructions may be presented indicating that the user is to lock the camera stand or camera, or has completed the positioning and orientation of the camera. In an example, a next operation may be registration of trackers within a surgical field using the camera.

Figure 4:
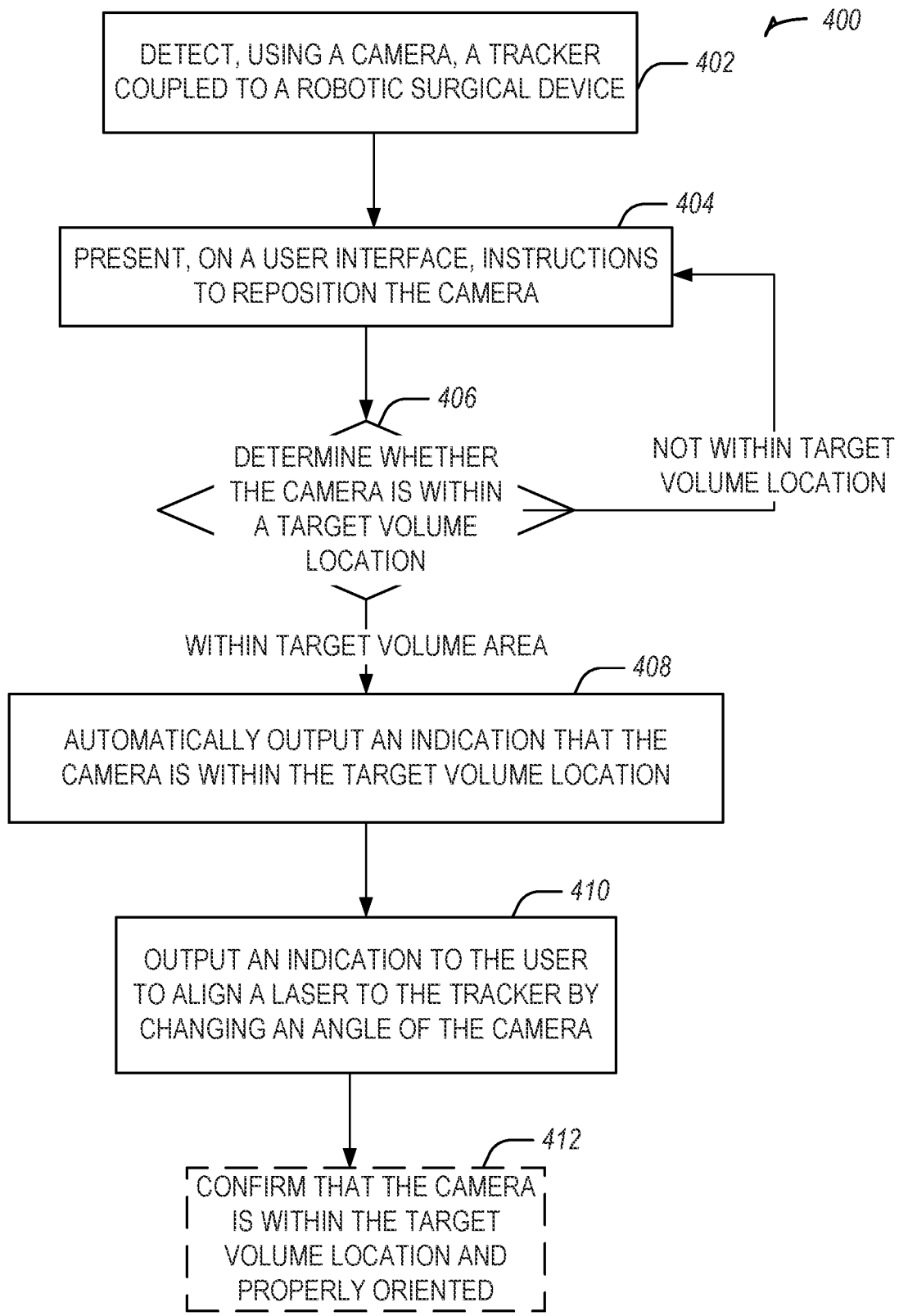
FIGS. 4-5 illustrate flowcharts showing techniques for positioning or orienting a camera within a surgical field in accordance with some embodiments.

FIG. 4 illustrates a flowchart illustrating an example of portions of a technique 400 for positioning or orienting a camera within a surgical field in accordance with some embodiments. The technique 400 includes an operation 402 to detect, such as using a camera, which may be on a camera stand, a tracker coupled to a robotic surgical device. Operation 402 may include detecting a tracker coupled to another object, such as a surgical table. The tracker may be referred to as a reference tracker. Other trackers may be used during a registration operation. The camera may be supported by a camera stand (e.g., coupled to the camera stand). The discussion with respect to technique 400 may include moving the camera stand instead of or in addition to the camera. In an example, the technique 400 may rely on known connections between the camera and the camera stand such that movement of one may be compensated, identified, or adjusted for later movement of the other.

The technique 400 includes an operation 404 to present, on a user interface, instructions to reposition the camera, the camera stand, or both. The user interface may include a first set of instructions to reposition the camera (e.g., move the camera or a camera stand), such as move forward, backward, left, right, etc. The technique 400 includes a decision operation 406 to determine whether the camera is within a target volume (e.g., at a particular location), When the camera is not within the target volume location, the technique 400 may return to operation 402 to present further instructions (e.g., direct the user towards the target volume). In an example, in response to determining that the camera is outside the target volume location, the technique 400 may include presenting a fourth set of instructions for display on the graphical user interface to reposition the camera.

When the camera is determined to be within the target volume area, the technique 400 may move to operation 408. The technique 400 includes an operation 408 to automatically output an indication that the camera is within the target volume location (e.g., in response to determining that the camera is within the target volume location). The technique 400 includes an operation 410 to output an indication to the user to align a laser to the tracker by changing an angle of the camera e.g., by providing instructions to rotate, tilt, or move the camera, such as up, down, left, right, etc.). The indication may further detail that the camera angle is to be changed for example, without moving the camera stand. The technique 400 includes an optional operation 412 to confirm that the camera is within the target volume location and properly oriented.

The technique 400 may include outputting a second indication to proceed to registration of the tracker. During registration, the technique 400 may include determining that the camera has moved. In response, the technique 400 may include issuing an alert that the camera has moved or pausing the registration. Determining that the camera has moved may include receiving tracking information for the tracker. The tracking information may indicate movement of the camera. In an example, the alert may include at least one of a visual alert on the graphical user interface, an audible alert, a haptic alert, or the like.

The technique 400 may include providing a third set of instructions for display on the graphical user interface to lock the camera stand supporting the camera or to lock the camera into place. The technique 400 may include accessing historical data including at least one parameter to determine the target volume location, wherein the at least one parameter is a user-specific (e.g., surgeon-specific), surgical procedure-specific, or particular operating room-specific parameter.

The technique 400 may include generating for display on the display device, a second graphical user interface including a top-down view of an operating room, including visual representations of the robotic surgical device, the camera, and the target volume location. In an example, the technique 400 may include determining the target volume location based on optical precision of the camera and one or more spatial constraints in an operating room containing the robotic surgical device and the camera. For example, the technique 400 may include calculating an error for at least one image of the tracker captured by the camera, determining whether the error falls below a threshold, then use a certain view volume of the camera, or in response to determining that the error falls below the threshold, modifying the first set of instructions for repositioning the camera. The technique 400 may include providing positioning instructions for the robotic surgical device before generating the first set of instructions to reposition the camera.

Figure 5:
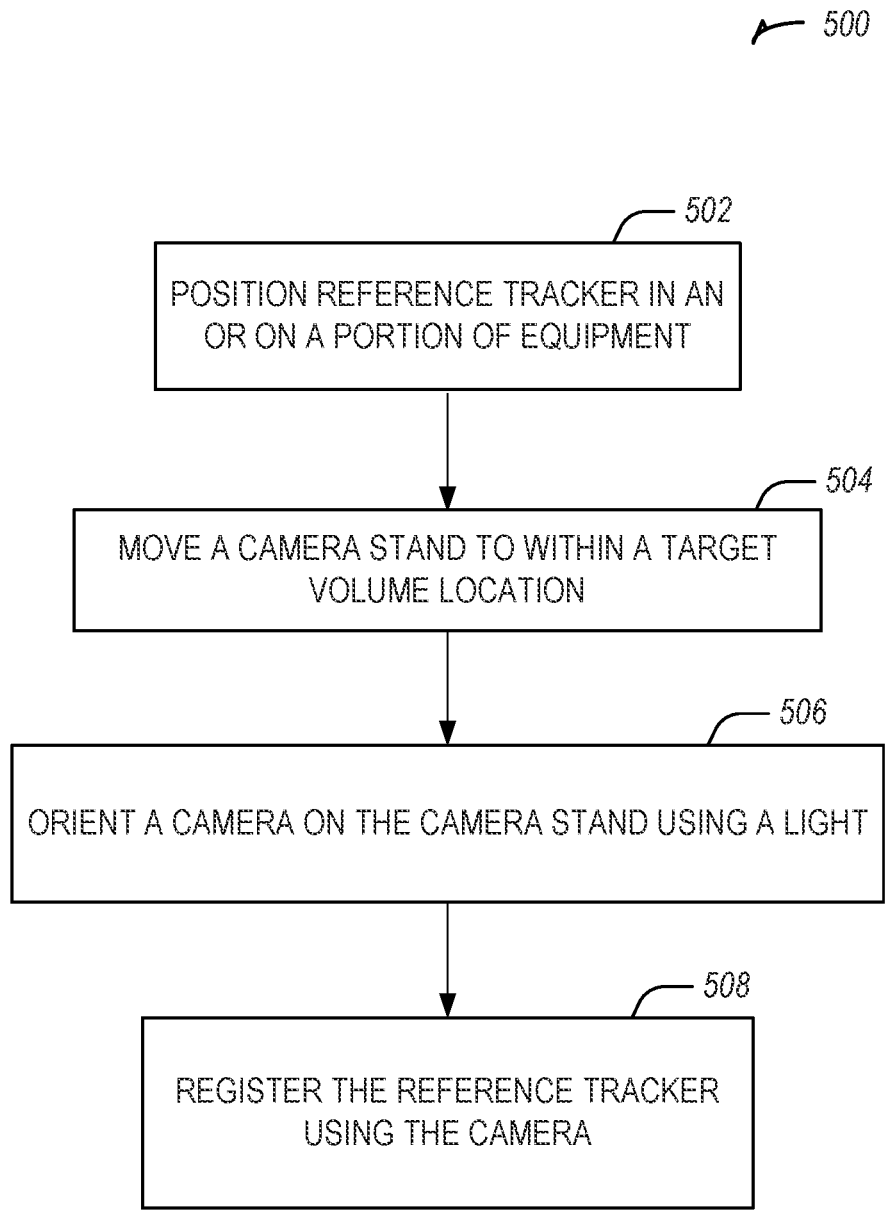

FIG. 5 illustrates a flowchart illustrating a technique 500 for positioning or orienting a camera within a surgical field in accordance with some embodiments. The technique 500 includes an operation 502 to position a reference tracker in or on a portion of equipment, such as an object, tool, instrument, robotic surgical device, etc. The reference tracker may be selected or placed such that it is to remain relatively static throughout a surgical procedure. In an example, the reference tracker may be already positioned, selected, or placed, and instead operation 502 may include activating the technique 500 (e.g., initiating a camera).

The technique 500 includes an operation 504 to move a camera stand to within a target volume location. The target volume may be previously selected based on attributes of the camera, a surgical field, a procedure, user-preferences, etc. The camera stand may be moved to within the target volume location automatically or by a user receiving instructions on a user interface, audibly, haptically, etc.).

The technique 500 includes an operation 506 to orient a camera on the camera stand using a light. The camera may be oriented using a laser. For example, a user may aim the laser at the reference tracker, thereby aligning the camera. The technique 500 includes an operation 508 to register the reference tracker using the camera Registering the reference tracker may include determining coordinates of the reference tracker within an optical tracking coordinate system. The coordinates may be converted to a robotic coordinate system for use with a robotic surgical device.

Figure 6:
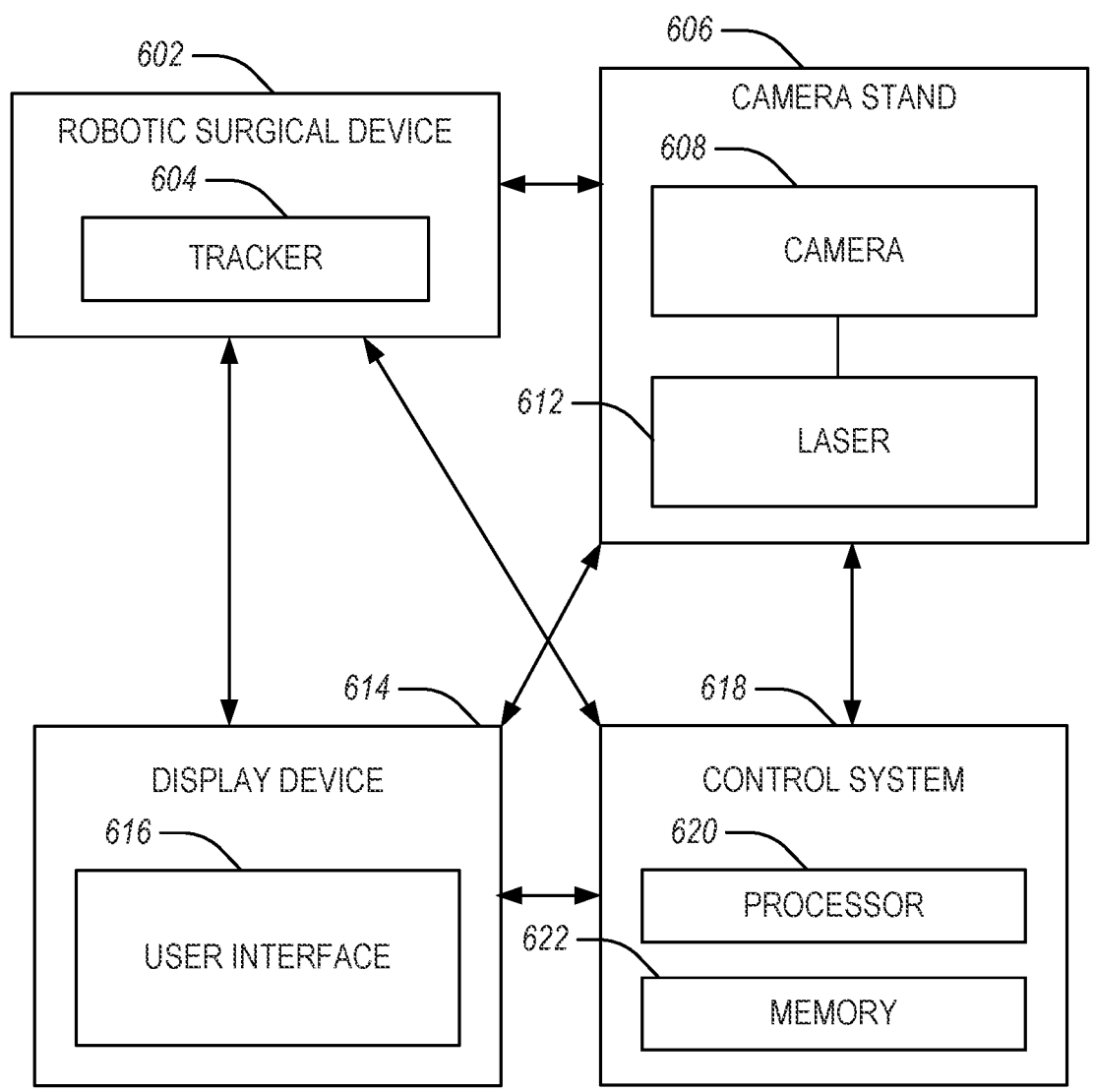
FIG. 6 illustrates a system for performing techniques described herein, in accordance with some embodiments.

FIG. 6 illustrates a system 600 for performing techniques described herein, in accordance with some embodiments. The system 600 includes a camera 608 affixed, embedded, or otherwise coupled to a camera stand 606. The system includes a robotic surgical device 602 coupled to a tracker 604, which may be used as a reference tracker for aligning the camera 608. The camera stand 606 includes a laser 612, which may be coupled to the camera 608. The system 600 may include a display device 614, which may be used to display a user interface 616. The system 600 may include a control system 618, including a processor 620 and memory 622. In an example, the display device 614 may be coupled to one or more of the robotic surgical device 602, the camera 608, the camera stand 606, or the control system 618.

The system 600 may be used to position or orient the camera 608 for a surgical procedure. For example, the camera 608 may be positioned (e.g., by moving the camera stand 606) within a target volume. The camera 608 may be oriented using the laser 612 to align the camera to the tracker 604.

In an example, the display device 614 may be used to display instructions on the user interface 616. The instructions may include directions for moving the camera 608 to within a target volume. After the camera 608 is within the target volume, the system 600 may automatically transition to an orientation operation. The user interface 616 may display instructions to a user to orient the camera 608 using the laser 612. The laser 612 may be pointed at the tracker 604 for alignment. In another example, the laser 612 may be aimed at some other portion of the robotic surgical device 602 or another object within a surgical field.

The system 600 may confirm that the camera 608 is within the target volume and oriented correctly. In an example, the user interface 616 may display instructions to a user to lock the camera 608 or the camera stand 606 into place after confirmation that the camera 608 is correctly positioned and oriented. In an example, the user interface 616 may include a button that a user may press to confirm that the camera 608 is correctly oriented. The system 600 may be used to register trackers within a surgical field after the camera 608 is correctly positioned and oriented.

Figure 7:
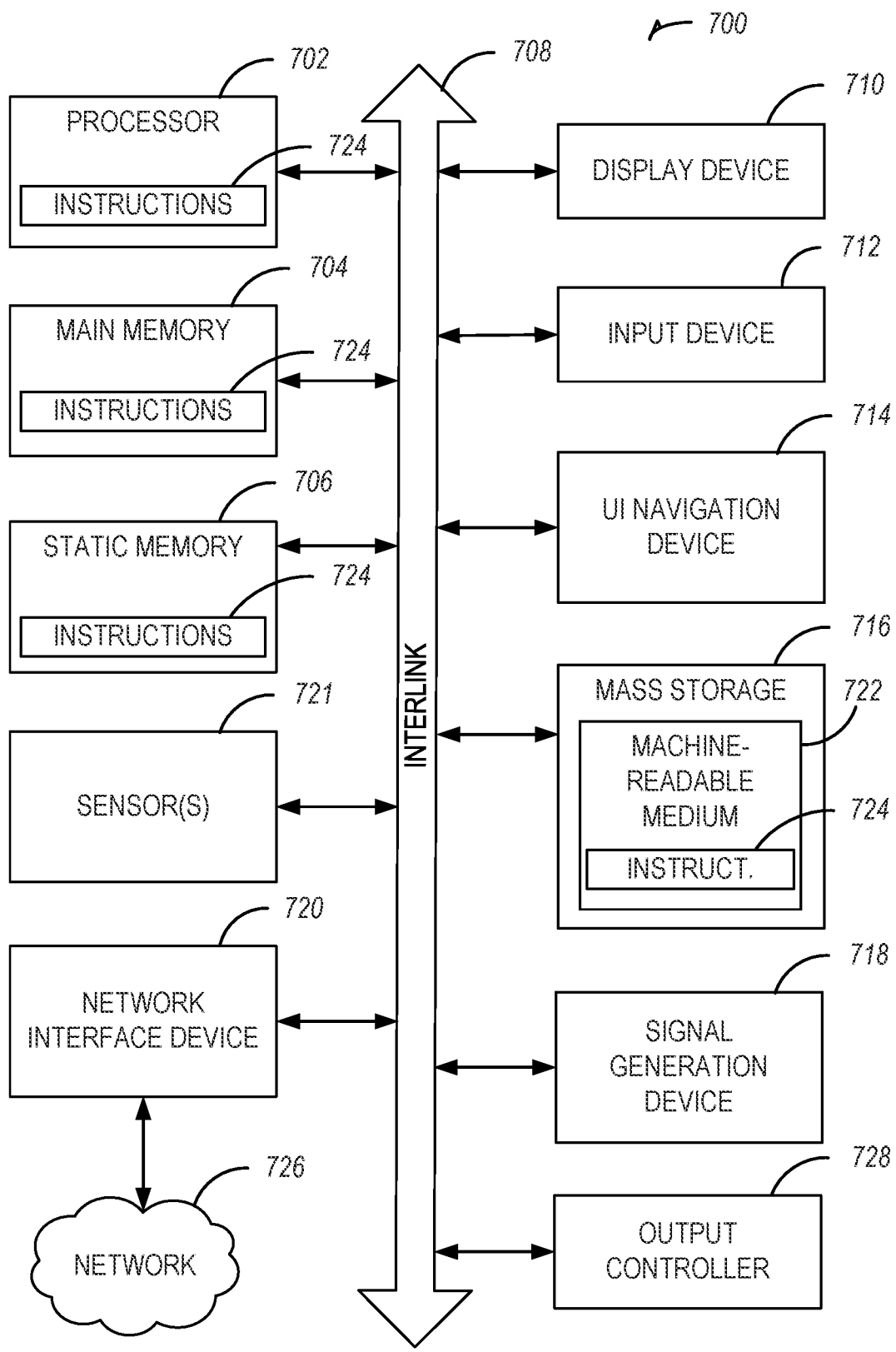
FIG. 7 illustrates a block diagram of an example of a machine upon which any one or more of the techniques discussed herein may perform in accordance with some embodiments.

FIG. 7 illustrates a block diagram of an example machine 700 upon which any one or more of the techniques discussed herein may perform in accordance with some embodiments. In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710, an alphanumeric input device 712. (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724. The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMaxg), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or oilier intangible medium to facilitate communication of such software.

VARIOUS NOTES & EXAMPLES

Each of these non-limiting examples may stand on its own, or may be combined in various permutations or combinations with one or more of the other examples.

Example 1 is a system comprising: a camera to detect a tracker coupled to a robotic surgical device; a display device; and processing circuitry coupled to memory, including processing instructions, which when executed by the processing circuitry, cause the processing circuitry to: generate a graphical user interface for presentation on the display device, the graphical user interface including a first set of instructions to reposition the camera; determine whether the camera is within a target volume location; in response to determining that the camera is within the target volume location, automatically output an indication that the camera is within the target volume location; output a second set of instructions for display on the graphical user interface to align a laser of the camera to the tracker by changing an angle of the camera; and optionally confirm that the camera is within the target volume location and properly oriented.

In Example 2, the subject matter of Example 1 includes, wherein the processing instructions further cause the processing circuitry to output a second indication to proceed to registration of the tracker.

In Example 3, the subject matter of Example 2 includes, wherein the processing instructions further cause the processing circuitry to, during the registration, determine that the camera has moved, issue an alert that the camera has moved, and pause the registration.

In Example 4, the subject matter of Example 3 includes, wherein to determine that the camera has moved includes receiving tracking information for the tracker, the tracking information indicating movement of the camera.

In Example 5, the subject matter of Examples 3-4 includes, wherein the alert includes at least one of a visual alert on the graphical user interface, an audible alert, or a haptic alert.

In Example 6, the subject matter of Examples 1-5 includes, wherein the processing instructions further cause the processing circuitry to provide a third set of instructions for display on the graphical user interface to lock a camera stand supporting the camera.

In Example 7, the subject matter of Examples 1-6 includes, wherein the processing instructions further cause the processing circuitry to, in response to determining that the camera is outside the target volume location, present a fourth set of instructions for display on the graphical user interface to reposition the camera.

In Example 8, the subject matter of Examples 1-7 includes, wherein the processing instructions further cause the processing circuitry to access historical data including at least one parameter to determine the target volume location, wherein the at least one parameter is a user-specific, surgical procedure-specific, or particular operating room-specific parameter.

In Example 9, the subject matter of Examples 1-8 includes, wherein the processing instructions further cause the processing circuitry to generate for display on the display device, a second graphical user interface including a top-down view of an operating room, including visual representations of the robotic surgical device, the camera, and the target volume location.

In Example 10, the subject matter of Examples 1-9 includes, wherein the processing instructions further cause the processing circuitry to determine the target volume location based on optical precision of the camera and one or more spatial constraints in an operating room containing the robotic surgical device and the camera.

In Example 11, the subject matter of Example 10 includes, wherein the processing instructions further cause the processing circuitry to: calculate an error for at least one image of the tracker captured by the camera; determine whether the error falls below a threshold, then use a certain view volume of the camera; and in response to determining that the error falls below the threshold, modify the first set of instructions for repositioning the camera.

In Example 12, the subject matter of Examples 1-11 includes, wherein the processing instructions further cause the processing circuitry to provide positioning instructions for the robotic surgical device before generating the first set of instructions to reposition the camera.

Example 13 is a system comprising: a camera to detect a tracker coupled to a robotic surgical device; a display device; and processing circuitry coupled to memory, including processing instructions, which when executed by the processing circuitry, cause the processing circuitry to: determine whether the camera is within a target volume location; in response to determining that the camera is not within the target volume location, generate a graphical user interface for presentation on the display device, the graphical user interface including a first set of instructions to reposition the camera; redetermine whether the camera is within a target volume location; in response to determining that the camera is within the target volume location, automatically output an indication that the camera is within the target volume location; output a second set of instructions for display on the graphical user interface to align a laser to the tracker by changing an angle of the camera; and optionally confirm that the camera is within the target volume location and properly oriented.

Example 14 is a system comprising: processing circuitry coupled to memory, including processing instructions, which when executed by the processing circuitry, cause the processing circuitry to: generate a graphical user interface for presentation on a display device, the graphical user interface including a first set of instructions to reposition the camera; determine whether a camera is within a target volume location; in response to determining that the camera is within the target volume location, automatically output an indication that the camera is within the target volume location; output a second set of instructions for display on the graphical user interface to align a laser of the camera to a tracker coupled to a robotic surgical device by changing an angle of the camera; and optionally confirm that the camera is within the target volume location and properly oriented.

Example 15 is a system comprising: processing circuitry coupled to memory, including processing instructions, which when executed by the processing circuitry, cause the processing circuitry to: generate a graphical user interface for presentation on a display device, the graphical user interface including a first set of instructions to reposition the camera; determine whether a camera is within a target volume location; in response to determining that the camera is within the target volume location, automatically output an indication that the camera is within the target volume location; and output a second set of instructions for display on the graphical user interface to align a laser of the camera to a tracker coupled to a robotic surgical device by changing an angle of the camera.

In Example 16, the subject matter of Examples 1-15 includes, wherein the processing instructions further cause the processing circuitry to confirm that the camera is within the target volume location and properly oriented.

Example 17 is a method comprising: detecting, using a camera, a tracker coupled to a robotic surgical device; generating, using a processor, a graphical user interface for presentation on a display device, the graphical user interface including a first set of instructions to reposition the camera; determining whether the camera is within a target volume location; in response to determining that the camera is within the target volume location, automatically outputting an indication that the camera is within the target volume location; outputting a second set of instructions for display on the graphical user interface to align a laser of the camera to the tracker by changing an angle of the camera; and optionally confirming that the camera is within the target volume location and properly oriented.

In Example 18, the subject matter of Example 17 includes, outputting a second indication to proceed to registration of the tracker.

In Example 19, the subject matter of Example 18 includes, during the registration, determine that the camera has moved, issue an alert that the camera has moved, and pause the registration.

In Example 20, the subject matter of Example 19 includes, wherein determining that the camera has moved includes receiving tracking information for the tracker, the tracking information indicating movement of the camera:

In Example 21, the subject matter of Examples 19-20 includes, wherein the alert includes at least one of a visual alert on the graphical user interface, an audible alert, or a haptic alert.

In Example 22, the subject matter of Examples 17-21 includes, providing a third set of instructions for display on the graphical user interface to lock a camera stand supporting the camera.

In Example 23, the subject matter of Examples 17-22 includes, in response to determining that the camera is outside the target volume location, presenting a fourth set of instructions for display on the graphical user interface to reposition the camera:

In Example 24, the subject matter of Examples 17-23 includes, accessing historical data including at least one parameter to determine the target volume location, wherein the at least one parameter is a user-specific, surgical procedure-specific, or particular operating room-specific parameter.

In Example 25, the subject matter of Examples 17-24 includes, generating for display on the display device, a second graphical user interface including a top-down view of an operating room, including visual representations of the robotic surgical device, the camera, and the target volume location.

In Example 26, the subject matter of Examples 17-25 includes, determining the target volume location based on optical precision of the camera and one or more spatial constraints in an operating room containing the robotic surgical device and the camera.

In Example 27, the subject matter of Example 26 includes, calculating an error for at least one image of the tracker captured by the camera; determining whether the error falls below a threshold, then use a certain view volume of the camera; and in response to determining that the error falls below the threshold, modifying the first set of instructions for repositioning the camera.

In Example 28, the subject matter of Examples 17-27 includes, providing positioning instructions for the robotic surgical device before generating the first set of instructions to reposition the camera.

Example 29 is a method comprising: detecting, using a camera, a tracker coupled to a robotic surgical device; determining, using a processor, whether the camera is within a target volume location; in response to determining that the camera is not within the target volume location, generating a graphical user interface for presentation on the display device, the graphical user interface including a first set of instructions to reposition the camera; redetermining whether the camera is within a target volume location; in response to determining that the camera is within the target volume location, automatically outputting an indication that the camera is within the target volume location; outputting a second set of instructions for display on the graphical user interface to align a laser to the tracker by changing an angle of the camera; and optionally confirming that the camera is within the target volume location and properly oriented.

Example 30 is a method comprising: generating, using a processor, a graphical user interface for presentation on a display device, the graphical user interface including a first set of instructions to reposition the camera; determining whether a camera is within a target volume location; in response to determining that the camera is within the target volume location, automatically outputting an indication that the camera is within the target volume location; outputting a second set of instructions for display on the graphical user interface to align a laser of the camera to a tracker coupled to a robotic surgical device by changing an angle of the camera; and optionally confirming that the camera is within the target volume location and properly oriented.

Example 31 is a method comprising: generating, using a processor, a graphical user interface for presentation on a display device, the graphical user interface including a first set of instructions to reposition the camera; determining whether a camera is within a target volume location; in response to determining that the camera is within the target volume location, automatically outputting an indication that the camera is within the target volume location; and outputting a second set of instructions for display on the graphical user interface to align a laser of the camera to a tracker coupled to a robotic surgical device by changing an angle of the camera.

In Example 32, the subject matter of Examples 17-31 includes, confirming that the camera is within the target volume location and properly oriented.

Example 33 is at least one machine-readable medium, including instructions, which when executed by processing circuitry, cause the processing circuitry to: detect, using information received from a camera, a tracker coupled to a robotic surgical device; generate a graphical user interface for presentation on a display device, the graphical user interface including a first set of instructions to reposition the camera; determine whether the camera is within a target volume location; in response to determining that the camera is within the target volume location, automatically output an indication that the camera is within the target volume location; output a second set of instructions for display on the graphical user interface to align a laser of the camera to the tracker by changing an angle of the camera; and optionally confirm that the camera is within the target volume location and properly oriented.

In Example 34, the subject matter of Example 33 includes, wherein the instructions further cause the processing circuitry to output a second indication to proceed to registration of the tracker.

In Example 35, the subject matter of Example 34 includes, wherein the instructions further cause the processing circuitry to, during the registration, determine that the camera has moved, issue an alert that the camera has moved, and pause the registration.

In Example 36, the subject matter of Example 35 includes, wherein to determine that the camera has moved includes receiving tracking information for the tracker, the tracking information indicating movement of the camera.

In Example 37, the subject matter of Examples 35-36 includes, wherein the alert includes at least one of a visual alert on the graphical user interface, an audible alert, or a haptic alert.

In Example 38, the subject matter of Examples 33-37 includes, wherein the instructions further cause the processing circuitry to provide a third set of instructions for display on the graphical user interface to lock a camera stand supporting the camera.

In Example 39, the subject matter of Examples 33-38 includes, wherein the instructions further cause the processing circuitry to, in response to determining that the camera is outside the target volume location, present a fourth set of instructions for display on the graphical user interface to reposition the camera.

In Example 40, the subject matter of Examples 33-39 includes, wherein the instructions further cause the processing circuitry to access historical data including at least one parameter to determine the target, volume location, wherein the at least one parameter is a user-specific, surgical procedure-specific, or particular operating room-specific parameter.

In Example 41, the subject matter of Examples 33-40 includes, wherein the instructions further cause the processing circuitry to generate for display on the display device, a second graphical user interface including a top-down view of an operating room, including visual representations of the robotic surgical device, the camera, and the target volume location.

In Example 42, the subject matter of Examples 33-41 includes, wherein the instructions further cause the processing circuitry to determine the target volume location based on optical precision of the camera and one or more spatial constraints in an operating room containing the robotic surgical device and the camera.

In Example 43, the subject matter of Example 42 includes, wherein the instructions further cause the processing circuitry to: calculate an error for at least one image of the tracker captured by the camera; determine whether the error falls below a threshold, then use a certain view volume of the camera; and in response to determining that the error falls below the threshold, modify the first set of instructions for repositioning the camera.

In Example 44, the subject matter of Examples 33-43 includes, wherein the instructions further cause the processing circuitry to provide positioning instructions for the robotic surgical device before generating the first set of instructions to reposition the camera.

Example 45 is at least one machine-readable medium, including instructions, which when executed by processing circuitry, cause the processing circuitry to: detect, using information received from a camera, a tracker coupled to a robotic surgical device; determine whether the camera is within a target volume location; in response to determining that the camera is not within the target volume location, generate a graphical user interface for presentation on a display device, the graphical user interface including a first set of instructions to reposition the camera; redetermine whether the camera is within a target volume location; in response to determining that the camera is within the target volume location, automatically output an indication that the camera is within the target volume location; output a second set of instructions for display on the graphical user interface to align a laser to the tracker by changing an angle of the camera, and optionally confirm that the camera is within the target volume location and properly oriented.

Example 46 is at least one machine-readable medium, including instructions, which when executed by processing circuitry, cause the processing circuitry to: generate a graphical user interface for presentation on a display device, the graphical user interface including a first set of instructions to reposition the camera; determine whether a camera is within a target volume location; in response to determining that the camera is within the target volume location, automatically output an indication that the camera is within the target volume location; output a second set of instructions for display on the graphical user interface to align a laser of the camera to a tracker coupled to a robotic surgical device by changing an angle of the camera; and optionally confirm that the camera is within the target volume location and properly oriented.

Example 47 is at least one machine-readable medium, including instructions, which when executed by processing circuitry, cause the processing circuitry to: generate a graphical user interface for presentation on a display device, the graphical user interface including a first set of instructions to reposition the camera; determine whether a camera is within a target volume location; in response to determining that the camera is within the target volume location, automatically output an indication that the camera is within the target volume location; and output a second set of instructions for display on the graphical user interface to align a laser of the camera to a tracker coupled to a robotic surgical device by changing an angle of the camera.

In Example 48, the subject matter of Examples 33-47 includes, wherein the instructions further cause the processing circuitry to confirm that the camera is within the target volume location and properly oriented.

Example 49 is at least one machine-readable medium including instructions that, when executed by processing circuitry, cause the processing circuitry to perform operations to implement of any of Examples 1-48.

Example 50 is an apparatus comprising means to implement of any of Examples 1-48.

Example 51 is a system to implement of any of Examples 1-48.

Example 52 is a method to implement of any of Examples 1-48,

Method examples described herein may be machine or computer-implemented at least in part, Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:
1. A system comprising:
a camera to detect a tracker coupled to a robotic surgical device;
a display device; and
processing circuitry coupled to memory, including processing instructions, which when executed by the processing circuitry, cause the processing circuitry to:
generate a graphical user interface for presentation on the display device, the graphical user interface including a first set of instructions to position the camera within the surgical field;
determine whether the camera is within a target volume location;
in response to determining that the camera is within the target volume location, automatically output an indication that the camera is within the target volume location;
output a second set of instructions for display on the graphical user interface to align a laser of the camera to the tracker by changing an angle of the camera; and
display a confirmation that the camera is within the target volume location and properly oriented.

2. The system of claim 1, further comprising instructions that cause the processing circuitry to generate the first set of instructions to position the camera based on a selected surgical procedure.

3. The system of claim 2, wherein the generating the first set of instructions to position the camera includes optimizing camera position and orientation based on minimizing line-of-sight obstructions anticipated during the selected surgical procedure.

4. The system of claim 1, further comprising instructions that cause the processing circuitry to generate the first set of instructions to position the camera based on an optical precision of the camera.

5. The system of claim 4, wherein the generating the first set of instructions to position the camera includes performing a precision analysis to determine the optical precision of the camera.

6. The system of claim 5, wherein performing the precision analysis includes determining a minimum and maximum distance for optimal performance of the camera.

7. The system of claim 1, further comprising instructions that cause the processing circuitry to generate the first set of instructions to position the camera based on training data for the target volume location, wherein the training data is generated based for a specific surgical procedure by optimizing location through testing a plurality of locations during a surgical procedure.

8. A method comprising:
generating, using a processor, a graphical user interface for presentation on a display device, the graphical user interface including a first set of instructions to position the camera within the surgical field, wherein the camera is configured to detect a tracker coupled to a surgical instrument;
determining whether the camera is within a target volume location;
in response to determining that the camera is within the target volume location, automatically outputting an indication that the camera is within the target volume location;
outputting a second set of instructions for display on the graphical user interface to align a laser associated with the camera to the tracker by changing an angle of the camera; and
displaying a confirmation that the camera is within the target volume location and properly oriented.

9. The method of claim 8, wherein generating the first set of instructions to position the camera is based receiving an indication of a selected surgical procedure.

10. The method of claim 9, wherein the generating the first set of instructions to position the camera includes optimizing camera position and orientation based on minimizing line-of-sight obstructions anticipated during the selected surgical procedure.

11. The method of claim 8, wherein generating the first set of instructions to position the camera is based on an optical precision of the camera.

12. The method of claim 11, wherein the generating the first set of instructions to position the camera includes performing a precision analysis to determine the optical precision of the camera.

13. The method of claim 12, wherein performing the precision analysis includes determining a minimum and maximum distance for optimal performance of the camera.

14. The method of claim 8, wherein generating the first set of instructions to position the camera is based on training data for the target volume location, wherein the training data is generated based on a specific surgical procedure by optimizing location through testing a plurality of locations during a surgical procedure.

15. At least one non-transitory machine-readable medium, including instructions, which when executed by processing circuitry, cause the processing circuitry to:
generate a graphical user interface for presentation on a display device, the graphical user interface including a first set of instructions to position the camera within the surgical field, wherein the camera is configured to detect a tracker coupled to a surgical instrument;
determine whether the camera is within a target volume location;
in response to determining that the camera is within the target volume location, automatically output an indication that the camera is within the target volume location;
output a second set of instructions for display on the graphical user interface to align a laser of the camera to the tracker by changing an angle of the camera; and
display a confirmation that the camera is within the target volume location and properly oriented.

16. The at least one non-transitory machine-readable medium of claim 15, further comprising instructions that cause the processing circuitry to generate the first set of instructions to position the camera based on a selected surgical procedure.

17. The at least one non-transitory machine-readable medium of claim 16, wherein the generating the first set of instructions to position the camera includes optimizing camera position and orientation based on minimizing line-of-sight obstructions anticipated during the selected surgical procedure.

18. The at least one non-transitory machine-readable medium of claim 15, further comprising instructions that cause the processing circuitry to generate the first set of instructions to position the camera based on an optical precision of the camera.

19. The at least one non-transitory machine-readable medium of claim 18, wherein the generating the first set of instructions to position the camera includes performing a precision analysis to determine the optical precision of the camera.

20. The at least one non-transitory machine-readable medium of claim 19, wherein performing the precision analysis includes determining a minimum and maximum distance for optimal performance of the camera.

21. The at least one non-transitory machine-readable medium of claim 15, further comprising instructions that cause the processing circuitry to generate the first set of instructions to position the camera based on training data for the target volume location, wherein the training data is generated based for a specific surgical procedure by optimizing location through testing a plurality of locations during a surgical procedure.

* * * * *